United States Patent
O'Hare et al.

(10) Patent No.: US 9,884,793 B2
(45) Date of Patent: *Feb. 6, 2018

(54) OLIGOMERISATION OF ETHYLENE

(71) Applicant: SCG Chemicals Co., Ltd., Bangkok (TH)

(72) Inventors: Dermot O'Hare, Oxford (GB); Jean-Charles Buffet, Oxford (GB); Zoe Turner, Oxford (GB)

(73) Assignee: SCG Chemicals Co., Ltd., Bangkok (TH)

( * ) Notice: Subject to any disclaimer, the term of this patent is extended or adjusted under 35 U.S.C. 154(b) by 0 days.

This patent is subject to a terminal disclaimer.

(21) Appl. No.: 15/310,812

(22) PCT Filed: May 13, 2015

(86) PCT No.: PCT/EP2015/060612
§ 371 (c)(1),
(2) Date: Nov. 14, 2016

(87) PCT Pub. No.: WO2015/173314
PCT Pub. Date: Nov. 19, 2015

(65) Prior Publication Data
US 2017/0088483 A1 Mar. 30, 2017

(30) Foreign Application Priority Data

May 15, 2014 (GB) .................................. 1408615.1

(51) Int. Cl.
C07C 2/30 (2006.01)
C07F 11/00 (2006.01)
C07C 2/34 (2006.01)
B01J 31/22 (2006.01)
C08F 210/16 (2006.01)

(52) U.S. Cl.
CPC ................. C07C 2/34 (2013.01); B01J 31/22 (2013.01); C08F 210/16 (2013.01); B01J 2231/20 (2013.01); B01J 2531/62 (2013.01); C07C 2531/22 (2013.01); C08F 2410/04 (2013.01)

(58) Field of Classification Search
CPC ..... C07C 2/30; C07C 2/06; C07C 2/08; C07F 11/00
See application file for complete search history.

(56) References Cited

U.S. PATENT DOCUMENTS

| 5,811,618 A | 9/1998 | Wu |
| 7,323,524 B2 | 1/2008 | Blann et al. |
| 8,716,456 B2 * | 5/2014 | O'Hare ................ B01J 31/2295 534/11 |
| 2002/0026016 A1 * | 2/2002 | Citron ..................... C08F 10/00 526/113 |
| 2008/0039600 A1 | 2/2008 | Bollmann et al. |
| 2010/0094070 A1 | 4/2010 | Qiu et al. |
| 2015/0246980 A1 * | 9/2015 | O'Hare ..................... C08F 4/80 502/107 |
| 2017/0022320 A1 * | 1/2017 | O'Hare ................. C08L 101/10 |

FOREIGN PATENT DOCUMENTS

CN 102453138 A 5/2012

OTHER PUBLICATIONS

International Search Report dated Dec. 8, 2015 from corresponding International Application No. PCT/EP2015/060612.
Small, Brooke L. et al., "New Chromium Complexes for Ethylene Oligomerization: Extended Use of Tridentate Ligands in Metal-Catalyzed Olefin Polymerization," Macromolecules 2004, 37, 4375-4386.
Summerscales, Owen T., et al. "The Organometallic Chemistry of Pentalene," Coordination Chemistry Reviews 250 (2006) 1122-1140.

* cited by examiner

Primary Examiner — Rip A Lee
(74) Attorney, Agent, or Firm — Foley Hoag LLP

(57) ABSTRACT

The present invention relates to a process for the oligomerisation of ethylene which comprises contacting ethylene with a transition metal-permethylpentalene complex, and a transition metal compound utilized therein.

16 Claims, 2 Drawing Sheets

OLIGOMERISATION OF ETHYLENE

RELATED APPLICATIONS

Figure 1:
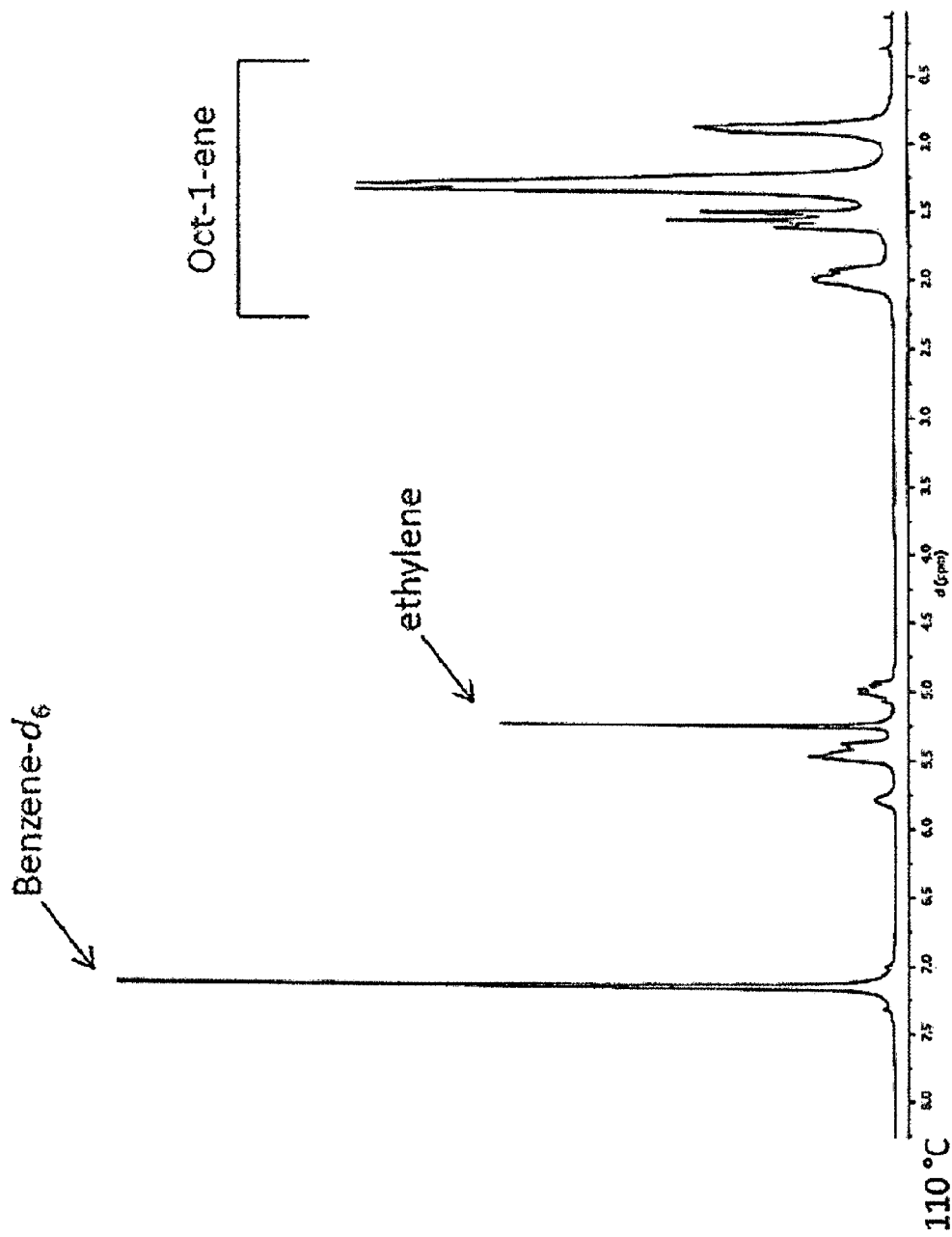

This application is a §371 national stage application based on Patent Cooperation Treaty Application serial number PCT/EP2015/060612, filed May 13,2015; which claims the benefit of priority to GB 1408615.1, filed May 15,2014.

The present invention relates to a process for the oligomerisation of ethylene, a transition metal compound utilized therein as catalyst and a composition comprising this transition metal compound immobilized on solid support material.

A process for the oligomerisation of an olefinic compound is disclosed in US 2008/0039600A. According to this, an olefinic compound in the form of an olefin or a compound including an olefinic moiety may be oligomerised by contacting the olefinic compound with at least two different catalysts, namely a tetramerisation catalyst and a further oligomerisation catalyst. The tetramerisation catalyst comprises a combination of a source of a transition metal; and a ligating compound of the formula

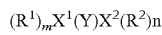

wherein: $X^1$ and $X^2$ are independently selected from the group consisting of N, P, As, Sb, Bi, O, S and Se; Y is a linking group between $X^1$ and $X^2$; m and n are independently 0, 1 or a higher integer; and $R^1$ and $R^2$ are independently hydrogen, a hydrocarbyl group, or a heterohydrocarbyl group, and $R^1$ being the same or different when m>1, and $R^2$ being the same or different when n>1, provided that (a) if two or more of $R^1$ and $R^2$ are aromatic with a ring atom of the aromatic ring structure bound to either $X^1$ or $X^2$, not more than two of said aromatic $R^1$ and $R^2$ have a substituent as a non-ring atom bound to a ring atom of the aromatic ring structure adjacent to the ring atom bound to $X^1$ or $X^2$; and (b) none of $R^1$ and $R^2$ are aromatic with a ring atom of the aromatic ring structure bound to either $X^1$ or $X^2$ and with a polar substituent as a non-ring atom bound to a ring atom of the aromatic ring structure adjacent to the ring atom bound to $X^1$ or $X^2$.

According to US 200810039600A, at least two different catalysts are required for the oligomerisation of the olefinic compound. Thus, not only is a tetramerisation catalyst, as defined above, required but a further oligomerisation catalyst is also required. According to US 2008/0039600A, the olefinic compound is contacted with the catalysts at a pressure of 100 kPa or higher, preferably greater than 1000 kPa, more preferably greater than 3000 kPa. Preferred pressure ranges, according to the disclosure in US 2008/0039600A, are from 1000 to 3000 kPa.

The preferred pressure ranges, according to the above-identified prior art document are high to very high.

Pentalenes and pentalene complexes are disclosed in WO 2008/110774.

Pentalene (formula $C_8H_6$; often abbreviated as "Pn") may be represented as having the structure

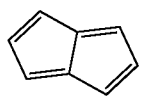

WO2008/110774 A2 discloses s substituted having the structure (I)

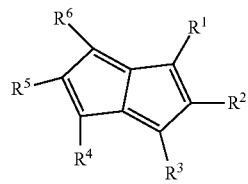

(I)

wherein $R^1$, $R^2$, $R^3$, $R^4$, $R^5$ and $R^6$ are each independently a substitutent group having up to 40 carbon atoms, provided that $R^1$, $R^2$, $R^3$, $R^4$, $R^5$ and $R^6$ are not each phenyl. According to one embodiment in WO-A-2008/110774, each of the $R^1$, $R^2$, $R^3$, $R^4$, $R^5$ and $R^6$ is a methyl group. Such a permethylpentalene is generally denoted as Pn* (formula $C_8Me_6$). Permethylpentalene derived ligands can be a protio form or anionic form (see examples figure below). The protio form such as hydro(permethylpentalene) denoted as Pn*H has the formula $C_8Me_6H$ as shown below. It can exist as neutral or anionic forms.

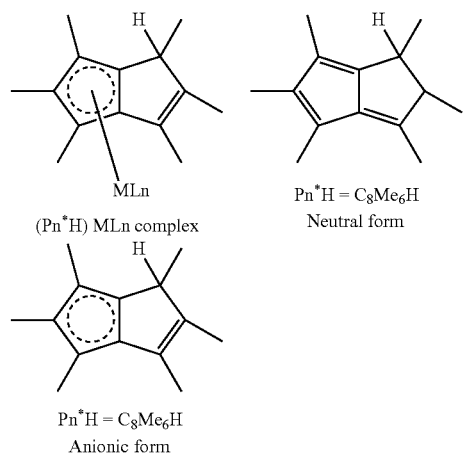

(Pn*H) MLn complex

Pn*H = $C_8Me_6H$
Neutral form

Pn*H = $C_8Me_6H$
Anionic form

Pn*H can form pi-complexes with metal centre (in particular transition metal centre) in which the ligand has an overall negative charge (see an example in the figure above).

WO-A-2008/110774 further discloses certain complexes incorporating one or more metal atoms or ions with one or more substituted pentalene ligands. The metal atoms or ion may be a transition metal (d block metal) or a lanthanide or actinide (f block metal). It may, instead, be an alkali or alkaline lo earth metal (s block metal) or a p block metal (e.g. Group 13 or 14 metal).

The complexes disclosed in WO-A-2008/110774 may be used to catalyse organic transformations selected from hydrogenation, hydroformylation, hydrosilylation, hydroamination, C—H bond activation, C—C bond formation, cyclotrimerisation, oxidation, epoxidation, dihydroxylation, and cycloadditions. The prior art complexes may also be used to catalyse a polymerisation, for example, olefinic polymerisation (e.g. the production of vinyl polymers), such as α-olefin polymerisation, and polymerisation of polar monomers (e.g. the polymerisation of caprolactone).

An object of the present invention is to provide a process for the oligomerisation of ethylene which overcomes the drawbacks of the prior art. A further object is to provide a process for the oligomerisation of ethylene using low ethylene pressures. A yet further object of the invention is to provide a novel compound which has use as a catalyst in the oligomerisation of ethylene.

The present invention is based on the surprising discovery that transition metal permethylpentalene derived complexes are useful as catalysts in the oligomerisation of ethylene and can be used to effect oligomerisation of ethylene, especially tetramerisation, under mild conditions such as at low ethylene pressures.

Accordingly, the present invention provides, in a first aspect, a process for the oligomerisation of ethylene which comprises contacting ethylene with a transition metal-(permethylpentalene) derived complex, preferably a transition metal-hydro(permethylpentalene) complex.

According to a second aspect, the present invention provides a compound having the formula [Pn*(H)CrCl$_2$]$_2$.

According to a third aspect, the present invention provides a composition comprising a compound having the formula [Pn*(H)CrCl$_2$]$_2$ immobilised on a solid support material.

Preferred embodiments are disclosed in the sub claims.

The process for the oligomerisation of ethylene, according to a first aspect, comprises contacting ethylene with a transition metal-permethylpentalene complex.

The oligomerisation reaction may be carried out in solution in a non-polar organic solvent. Examples of suitable non-polar organic solvents include liquid hydrocarbons, examples of which include benzene and lower alkyl-substituted benzenes. The transition metal-permethylpentalene derived complex may be immobilised on a suitable solid support material and the reaction may be carried out in a slurry of the immobilised complex in a non-polar organic solvent such as a hydrocarbon.

The oligomerisation catalyst used in the process of the present invention is, as stated above, a transition metal-permethylpentalene ligand derived complex. The transition metal may be a d block metal. Preferably, the transition metal is chromium. The chromium is typically associated with one or more anions, such as halogen anions, especially chloride ions. According to a particularly preferred embodiment, the oligomerisation catalyst used in the process of the invention has the formula [Pn*(H)CrCl$_2$]$_2$, wherein Pn* represents permethylpentalene (C$_8$Me$_6$) as shown below.

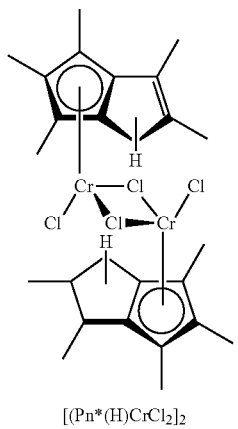

[(Pn*(H)CrCl$_2$]$_2$

The use of the transition metal-permethylpentalene derived complex, as oligomerisation catalyst, makes it possible to obtain oligomers of ethylene using mild reaction conditions. Preferably, the oligomerisation is a trimerisation or tetramerisation of ethylene. In another preferred embodiment, the present invention also relates to a process for the manufacture of an ethylene-olefin copolymer using a composition according to the present invention as a first catalyst in combination with an ethylene polymerisation catalyst as a second catalyst.

In particular, only low ethylene pressures are required in order to obtain oligomers. Typically, an ethylene pressure of less than 1000 kPA (10 atm) is used in the reaction. Preferably, the ethylene pressure will be about 200 kPa (approx. 2 atm). Typically, the temperature of reaction will be in the range of from 75° to 120° C., preferably 80° C. to 110° C. Reaction times may range from 30 minutes to several hours, typically 1 to 5 hours.

The preferred oligomerisation catalyst used in the process of the invention is, as stated above, the compound [Pn*(H)CrCl$_2$]$_2$ Accordingly, in a different aspect, the present invention provides a chromium-hydro(permethylpentaiene) complex having the formula [Pn*(H)CrCl$_2$]$_2$.

The present invention further provides a composition for use in the oligomerisation of ethylene which comprises the compound [Pn*(H)CrCl$_2$]$_2$ immobilised on a solid support. Typically, the solid support material will be an inorganic oxide or inorganic hydroxide, for example silica, alumina or a layered double hydroxide, which may be thermally or optionally solvent treated.

Layered double hydroxides (LDHs) are a class of compounds which comprise at least two metal cations and have a layered structure. A brief review of LDHs is provided in *Chemistry in Britain*, Sep. 1997, pages 59 to 62. The hydrotalcites, perhaps the most well-known examples of LDHs, have been studied for many years.

LDHs can be represented by the general formula $[M^{II}_{(1-x)}M^{III}_x(OH)_2]^{x+}(A^{z-})_{x/z} \cdot yH_2O \cdot w(\text{solvent})$ or $[M^{I}_{(1-x)}M^{III}_x(OH)_2]^{n+}(A^{z-})_{n/z} \cdot yH_2O \cdot w(\text{solvent})$, where $M^I$, $M^{II}$ and $M^{III}$ are mono, di and trivalent metal cations respectively, that occupy octahedral positions in hydroxide layers, $A^{z-}$ is an interlayer charge-compensating anion, where z is an integer, n=2x−1, x is a number less than 1 and y is 0 or a number greater than 0, solvent is 100% v miscible in water and is typically acetone or methanol, w=0.1. Examples of $A^{z-}$ include $CO_3^{2-}$, $NO_3^-$ and $Cl^-$. A large number of LDHs with a wide variety of $M^I$-$M^{III}$ cation pairs (e.g., Mg—Al, Ca—Al) as well as the $M^I$-$M^{III}$ cation pair (Li—Al) with different anions in the interlayer space have been reported and studied. Preferred layered double hydroxides, for use as solid support material for the catalytic compounds as those having the general formula

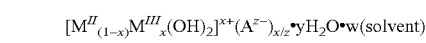

in which $M^{II}$ is a divalent metal cation;
$M^{III}$ is a trivalent metal cation;
A is a counter anion; and
x is a number less than 1, w is a number less than 1, y is 0 or a number greater than 0, z is an integer which gives compounds optionally hydrated with a stoichiometric amount or a non-stoichiometric amount of water and/or an aqueous-miscible organic solvent (AMO-solvent), such as acetone.

Preferably, in the LDH of the above formula, $M^{II}$ is Mg or Ca and $M^{III}$ is Al. The counter anion A is typically selected from $CO_3^{2-}$, $OH^-$, $F^-$, $Cl^-$, $Br^-$, $I^-$, $SO_4^{2-}$, $NO_3^-$ and $PO_4^{3-}$. According to a preferred embodiment, the LDH used as a solid support material will be one wherein $M^{II}$ is Mg, $M^{III}$ is Al and A is $CO_3^{2-}$. The BET surface of the LDHs is typically greater than 100 m$^2$g$^{-1}$.

In an even preferred embodiment, the LDH used as support material may have the formula

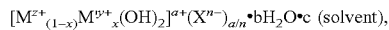

wherein M and M' are two different charged metal cations, wherein M may be a mixture of one or more metal cations of charge z and M' may be a mixture of one or more metal cations of charge y, z=1 or 2; y=3 or 4; 0<x<0.9; b is 0 to 10; c is 0 to 10; X is an anion with n>0, preferably 1-5; a=z(1−x)+xy−2, wherein the solvent is preferably an aqueous miscible organic solvent. Preferably, in the LDH of the above formula, M is Mg or Ca, and M' is Al. The counter anion X is typically selected from $CO_3^{2-}$, $OH^-$, $F^-$, $Cl^-$, $Br^-$, $I^-$, $SO_4^{2-}$, $NO_3^-$ and $PO_4^{3-}$. According to a preferred embodiment, the LDH used as a solid support material will be one wherein M is Mg, M' is Al and X is $CO_3^{2-}$. The BET surface of the LDH is typically greater than 100 $m^2g^{-1}$.

The solid support material may be activated with an activator compound, such as an alkylaluminoxane, for example methylaluminoxane. According to one preferred embodiment, the solid support material is silica treated with methylaluminoxane. According to a different preferred embodiment, the solid support material is a layered double hydroxide treated with methylaluminoxane.

Further advantages and features of the subject-matter of the present invention can be taken from the following detailed examples section illustrating preferred embodiments, which are not to be taken as limiting the scope of protection which is only defined by the appending claims.

The invention is illustrated by the drawings in which:

FIG. 1: $^1H$ NMR spectroscopy (298K, benzene-$d_6$) of oligomerisation of ethylene using $[Pn^*(H)CrCl2]_2$ FIG. 2: GC Chromatogram (298K, dichloromethane) of the oligomerisation of ethylene using $[Pn^*(H)CrCl2]_2$

EXAMPLE (A) Synthesis of $[Pn^*(H)CrCl_2]_2$
  To a slurry of $CrCl_3$ (0.0981 g, 0.619 mmole) in benzene was added a solution of $Pn^*(H)SnMe_3$ (0.218 g, 0.619 mmole) in benzene. The reaction mixture was heated to 80° C. for 5 days to afford a dark-green solution. The reaction mixture was filtered and the volatiles were removed in vacuo to afford a dark-green powder which was washed with pentane and dried under reduced pressure to yield $[Pn^*(H)CrCl_2]_2$ as a dark-green powder. The complex is paramagnetic. The yield was 67%.
(B) Characterisation of $[Pn^*(H)CrCl_2]_2$
  $^1H$ NMR spectrum ($C_6D_6$, 23° C.) δ=range of −36.0-18.3 ppm.
(C) Oligomerisation of Ethylene
(1) The complex $[(Pn^*(H)CrCl_2]_2$ was dissolved in benzene-$d_6$ and the solution was maintained at a temperature of 110° C. Ethylene was supplied under a pressure of 200 kPa into the solution for one hour. The resulting solution was subjected to $^1H$ NMR spectroscopy (298 K, benzene-$d_6$) to study the products of the oligomerisation reaction. The $^1H$ NMR spectrum is shown in FIG. 1. The $^1H$ NMR spectrum indicates the presence of only oct-1-ene.
(2) The complex $[Pn^*(H)CrCl_2]_2$ was also used in solution in toluene to catalyse the oligomersiation of ethylene at a temperature of 80° C. for 2 hours at 200 kPa.

Figure 2:
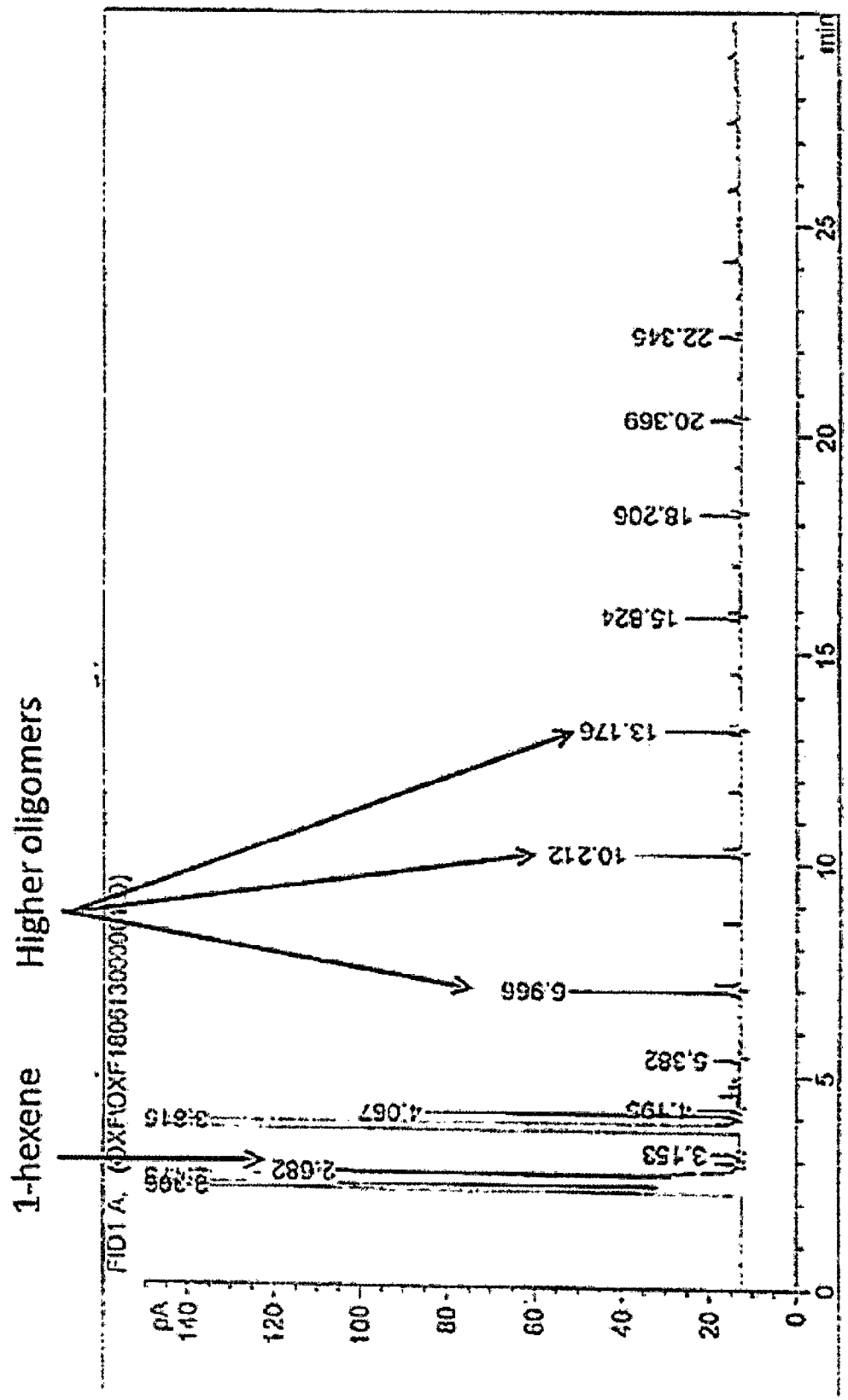

FIG. 2 shows a GC chromatogram (298 K, dichloromethane) of the oligomerisation. FIG. 2 highlights the presence of 1-hexene and higher oligomers.

The above examples for oligomerisation indicate that utilizing the transition metal-permethyl penthalene derived complex in the oligomerisation of ethylene provides an extremely selective oligomerisation, only 1-octene was produced in example 1.

The features disclosed in the foregoing description, in the claims and in the accompanying drawings may both separately or in any combination be material for realizing the invention in diverse forms thereof.

The invention claimed is:

1. A process for the oligomerisation of ethylene which comprises contacting ethylene with a transition metal-hydro (permethylpentalene) complex.

2. The process according to claim 1, wherein the transition metal is chromium.

3. The process according to claim 1, wherein the process is carried out in solution in a non-polar organic solvent.

4. The process according to claim 1, wherein the transition metal-hydro(permethylpentalene) complex is immobilised on a solid support material to provide an immobilised complex, and wherein the process is carried out in a slurry of the immobilised complex in a non-polar organic solvent.

5. The process according to claim 3, wherein the non-polar organic solvent is a liquid hydrocarbon.

6. The process according to claim 1, wherein ethylene is supplied at a pressure of less than 10 atm.

7. The process according to claim 6, wherein ethylene is supplied at a pressure of 2 atm.

8. The process according to claim 1, wherein the transition metal-hydro(permethylpentalene) complex is a complex of chromium and hydro(permethylpentalene) having the formula $[Pn^*(H)CrCl_2]_2$, wherein $Pn^*$ is a permethylpentalene moiety.

9. A compound having the formula $[Pn^*(H)CrCl_2]_2$, wherein $Pn^*$ is a permethylpentalene moiety.

10. A composition comprising the compound according to claim 9 immobilised on a solid support material.

11. The composition according to claim 10, wherein the solid support material comprises silica treated with methylaluminoxane.

12. The composition according to claim 10, wherein the solid support material comprises a layered double hydroxide treated with methylaluminoxane.

13. A method of making 1-octene or 1-hexene which comprises contacting ethylene with a transition metal-hydro (permethylpentalenel) complex.

14. A method of making an ethylene-olefin copolymer, the method comprising the step of contacting ethylene with a composition according to claim 10 as a first catalyst, wherein the composition is provided in combination with an ethylene polymerization catalyst as a second catalyst.

15. The composition according to claim 10, wherein the solid support material is silica treated with methylaluminoxane.

16. The composition according to claim 10, wherein the solid support material is a layered double hydroxide treated with methylaluminoxane.

* * * * *